United States Patent [19]

Senzaki et al.

[11] Patent Number: 5,767,301

[45] Date of Patent: Jun. 16, 1998

[54] PRECURSOR WITH (ALKYLOXY)(ALKYL)-SILYLOLEFIN LIGAND TO DEPOSIT COPPER

[75] Inventors: Yoshihide Senzaki; Masato Kobayashi; Lawrence J. Charneski; Tue Nguyen, all of Vancouver, Wash.

[73] Assignees: Sharp Microelectronics Technology, Inc., Camas, Wash.; Sharp Kabushiki Kaisha, Osaka, Japan

[21] Appl. No.: 786,546

[22] Filed: Jan. 21, 1997

[51] Int. Cl.$^6$ .................................. C07F 1/08; C07F 7/18
[52] U.S. Cl. ........................ 556/9; 556/117; 556/12; 116/1.25; 117/104; 427/587
[58] Field of Search .......................... 556/9, 12, 117; 116/1.25; 117/104; 427/587

[56] References Cited

U.S. PATENT DOCUMENTS

| | | | |
|---|---|---|---|
| 5,028,724 | 7/1991 | Ivankovits et al. | 556/40 |
| 5,085,731 | 2/1992 | Norman et al. | 156/646 |
| 5,096,737 | 3/1992 | Baum et al. | 427/38 |
| 5,098,516 | 3/1992 | Norman et al. | 156/666 |
| 5,144,049 | 9/1992 | Norman et al. | 556/12 |
| 5,187,300 | 2/1993 | Norman | 556/12 |
| 5,322,712 | 6/1994 | Norman et al. | 427/250 |
| 5,663,391 | 9/1997 | Machida et al. | 556/12 |

OTHER PUBLICATIONS

Norman et al., Chemical Abstracts, Vo. 119, No. 6, abstract No. 60602h, p. 813, Aug. 1993.

Article entitled, "Chemical Additives for Improved Copper Chemical Vapour Deposition Processing" by J. Norman, D. Roberts, A. Hochberg, R. Smith, G. Petersen, J. Parmeter, C. Apblett, T. Omstead in the Thin Solid Films 262 (1995) pp. 46–51.

Article entitled, "MOCVD of Copper from New and Liquid Precursors (hfac)CuL, Where L=1-Pentene, ARMS, and VTMOS", by H.K. Shin, H.J. Shin, S.J. Lim, D.J. Yoo, N.Y. Oh, H.J.Yoo, J.T.Baek, C.H. Jun, & Y.T. Kim in the Material Res. Soc. Symp. Proc. vol. 427, 1996 Materials Research Society, pp. 219–223.

Article entitled, "Ligand–Stabilized Copper (I) Hexafluoracetylacetonate Complexes: NMR Spectroscopy and the Nature of the Copper–Alkene Bond" by T. Baum, C. Larson and G. May, published in Journal of Organometallic Chemistry, 425 (1992) pp. 189–200.

Article entitled, "The Effect of Adding Hexafluoracetylacetone on Chemical Vapor Deposition of Copper Using cu(I) and Cu(II) Precursor Systems", by N. Awaya, K. Ohno and Y. Arita, published in J. Electrochem. Soc. vol. 142, No. 9, Sep. 1995, pp. 3173–3179.

Article entitled, Chemical Vapor Deposition of Copper from Hexafluoracetylacetonato Copper(I) Vinyltrimethylsilane, Deposition Rates, Mehaism, Selectivity, Morphology & Resistivity as a Function of Temperature and Pressure by A. Jain, K.M. Chi, T.T. Kodas & M.J. Hampden–Smith, published in J. Electrochem Soc. vol. 140, No. 5, May 1993, pp. 1434–1439.

Article entitled, Chemical Additives for Improved Copper CVD Processing Using (hfac) Cu(TMVS) by A. Hochberg, J. Norman and D. Roberts, published in Conference Proceedings ULSI-X, 1995 Materials Reserach Society, pp. 79–86.

Article entitled, "A Stable, Liquid Precursor for Aluminum" by M. G. Simmonds, E. C. Phillips, J-W Hwang & W.L. Gladfelter, published in Chemtronics, vol. 5, 1991, pp. 155–158.

*Primary Examiner*—Porfirio Nazario-Gonzalez
*Attorney, Agent, or Firm*—Gerald Maliszewski; David C. Ripma

[57] ABSTRACT

A method is provided for applying chemical vapor deposition (CVD) copper (Cu) to integrated circuit substrates using a Cu(hfac)(ligand) precursor with a silylolefin ligand including combinations of C1–C8 alkyl groups with at least one C2–C8 alkyloxy group. The alkyloxy groups include, ethoxy, propoxy, butoxy, pentyloxy, hexyloxy, heptyloxy, octyloxy, and aryloxy, while the alkyl groups include methyl, ethyl, propyl, butyl, pentyl, hexyl, heptyl, octyl, and aryl. The oxygen atoms of the alkyloxy groups, and the long carbon chains of both the alkyl and alkyloxy groups, increase the stability of the precursor by contributing electrons to the Cu(hfac) complex. The improved bond helps insure that the ligand separates from the (hfac)Cu complex at consistent temperatures when Cu is to be deposited. Combinations of alkyloxy and alkyl groups allow the molecular weight of the precursor to be manipulated so that the volatility of the precursor is adjustable for specific process scenarios. Other embodiments provide a precursor blend made from additional silylolefins, hexafluoroacetylacetone (H-hfac), H-hfac dihydrate, and water, either separately, or in combinations, to enhance deposition rate, conductivity, and precursor stability. A Cu precursor compound including silylolefin ligands having at least one alkyloxy group is also provided. Combinations of ethyl groups with ethoxy groups are specifically disclosed.

29 Claims, 4 Drawing Sheets

PRECURSOR WITH (ALKYLOXY)(ALKYL)-SILYLOLEFIN LIGAND TO DEPOSIT COPPER

BACKGROUND AND SUMMARY OF THE INVENTION

This invention relates generally to integrated circuit processes and fabrication, and more particularly, to a precursor and method, having enhanced temperature stability, used to deposited copper on selected integrated circuit surfaces.

The demand for progressively smaller, less expensive, and more powerful electronic products, in turn, fuels the need for smaller geometry integrated circuits (ICs) on larger substrates. It also creates a demand for a denser packaging of circuits onto IC substrates. The desire for smaller geometry IC circuits requires that the interconnections between components and dielectric layers be as small as possible. Therefore, research continues into reducing the width of via interconnects and connecting lines. The conductivity of the interconnects is reduced as the area of the interconnecting surfaces is reduced, and the resulting increase in interconnect resistivity has become an obstacle in IC design. Conductors having high resistivity create conduction paths with high impedance and large propagation delays. These problems result in unreliable signal timing, unreliable voltage levels, and lengthy signal delays between components in the IC. Propagation discontinuities also result from intersecting conduction surfaces that are poorly connected, or from the joining of conductors having highly different impedance characteristics.

There is a need for interconnects and vias to have both low resistivity, and the ability to withstand process environments of volatile ingredients. Aluminum and tungsten metals are often used in the production of integrated circuits for making interconnections or vias between electrically active areas. These metals are popular because they are easy to use in a production environment, unlike copper which requires special handling.

Copper (Cu) would appear to be a natural choice to replace aluminum in the effort to reduce the size of lines and vias in an electrical circuit. The conductivity of copper is approximately twice that of aluminum and over three times that of tungsten. As a result, the same current can be carried through a copper line having nearly half the width of an aluminum line.

The electromigration characteristics of copper are also much superior to those of aluminum. Aluminum is approximately ten times more susceptible than copper to degradation and breakage due to electromigration. As a result, a copper line, even one having a much smaller cross-section than an aluminum line, is better able to maintain electrical integrity.

There have been problems associated with the use of copper, however, in IC processing. Copper pollutes many of the materials used in IC processes and, therefore barriers are typically erected to prevent copper from migrating. Elements of copper migrating into these semiconductor regions can dramatically alter the conduction characteristics of associated transistors. Another problem with the use of copper is the relatively high temperature needed to deposit it on, or removing it from, an IC surface. These high temperatures can damage associated IC structures and photoresist masks.

It is also a problem to deposit copper onto a substrate, or in a via hole, using the conventional processes for the deposition of aluminum when the geometries of the selected IC features are small. That is, new deposition processes have been developed for use with copper, instead of aluminum, in the lines and interconnects of an IC interlevel dielectric. It is impractical to sputter metal, either aluminum or copper, to fill small diameter vias, since the gap filling capability is poor. To deposit copper, first, a physical vapor deposition (PVD), and then, a chemical vapor deposition (CVD) technique, have been developed by the industry.

With the PVD technique, an IC surface is exposed to a copper vapor, and copper is caused to condense on the surfaces. The technique is not selective with regard to surfaces. When copper is to be deposited on a metallic surface, adjoining non-conductive surfaces must either be masked or etched clean in a subsequent process step. As mentioned earlier, photoresist masks and some other adjoining IC structures are potentially damaged at the high temperatures at which copper is processed. The CVD technique is an improvement over PVD because it is more selective as to which surfaces copper is deposited on. The CVD technique is selective because it is designed to rely on a chemical reaction between the metallic surface and the copper vapor to cause the deposition of copper on the metallic surface.

In a typical CVD process, copper is combined with a ligand, or organic compound, to help insure that the copper compound becomes volatile, and eventually decomposes, at consistent temperatures. That is, copper becomes an element in a compound that is vaporized into a gas, and later deposited as a solid when the gas decomposes. Selected surfaces of an integrated circuit, such as diffusion barrier material, are exposed to the copper gas, or precursor, in an elevated temperature environment. When the copper gas compound decomposes, copper is left behind on the selected surface. Several copper gas compounds are available for use with the CVD process. It is generally accepted that the configuration of the copper gas compound, at least partially, affects the ability of the copper to be deposited on to the selected surface.

$Cu^{+2}(hfac)_2$, or copper (II) hexafluoroacetylacetonate, precursors have previously been used to apply CVD copper to IC substrates and surfaces. However, these $Cu^{+2}$ precursors are notable for leaving contaminates in the deposited copper, and for the relatively high temperatures that must be used to decompose the precursor into copper. Currently, more success has been found with the use of $Cu^{+1}(hfac)$ compounds to apply copper. Norman, et al., U.S. Pat. No. 5,322,712, discloses a (hfac)Cu(tmvs), or copper hexafluoroacetylacetonate trimethylvinylsilane, precursor that is the industry standard at the time of this writing. Alternately, tmvs is known as vtms, or vinyltrimethylsilane. This precursor is useful because it can be used at relatively low temperatures, approximately 200° C. In addition, the film resisitivity of copper applied with this method is very good, approaching the physical limit of 1.7 $\mu\Omega$-cm. However, the adhesiveness between copper deposited with this precursor and the surface to which it is deposited is not always good. Also, the precursor is not especially stable, and can have a relatively short shelf life if not refrigerated. Various ingredients have been added to (hfac)Cu(tmvs) to improve its adhesiveness, temperature stability, and the rate at which it can be deposited on an IC surface. A co-pending application Serial No. 08/745,562 filed Nov. 8, 1996, entitled "Cu(hfac) TMVS Precursor With Water Additive To Increase The Conductivity Of Cu And Method For Same", invented by Nguyen et al., Attorney Docket No. SMT 244, and assigned to the same assignee as the instant patent, discloses a precursor and method of improving the electrical conductivity of Cu deposited with (hfac)Cu(tmvs).

It is generally acknowledged in the industry that (hfac) Cu(tmvs) becomes unstable, and begins to decompose, above 35° C. Use of a (hfac)Cu(tmvs) precursor stored at this temperature leads to undesirable process results. Typically, the precursor is a liquid at room temperature, and must be converted to a vapor form. In interacting with a heated target surface, the vaporized precursor first cleaves the tmvs ligand, and then the hfac, leaving Cu on the target surface. During this process a disproportionation reaction occurs in which uncharged atoms of Cu are left on the surface, while volatile forms of $Cu+^2(hfac)_2$ and the tmvs ligand are exhausted through the system.

As an unstable precursor is heated to a vapor, the tmvs ligand cleaves unevenly from the precursor, some cleavage, or decomposition, occurs at low temperature, and some at higher temperatures. Because the precursor decomposes at low temperatures, the precursor vacuum pressure, or partial pressure, remains undesirably low, resulting in low Cu deposition rates, uneven surfaces, and variances in surface conductances. The effectivity of (hfac)Cu(tmvs) stored at temperatures lower than 35° C. is also unpredictable. A "fresh" batch of precursor, or precursor stored at temperatures well below room temperature, is used to guarantee predictable processes.

Various additives have been mixed with the (hfac)Cu (tmvs) precursor to improve its temperature stability. It is well known to blend hexafluoroacetylacetone (H-hfac), tmvs, and other chemical agents to improve temperature stability. Baum et al., in "Ligand-stabilized copper(I) hexafluoroacetylacetonate complexes: NMR spectroscope and the nature of the copper-alkene bond", J. Organomet. Chem., 425, 1992, pp. 189–200, disclose alkene groups affecting improvement in the stability of Cu precursors. They also qualitatively analyze the nature of sigma and pi bonds in the Cu-alkene bond of a (hfac)Cu(alkene) complex.

Choi et al., in "Chemical vapor deposition of copper with a new metalorganic source", Appl. Phys. Lett. 68 (7), 12 Feb. 1996, pp. 1017–1019, disclose trimethoxyvinylsilane (tmovs) as a ligand to improve the temperature stability of $Cu^{+1}$ complexes. Using the tmovs ligand, precursor stability up to the temperature of 70° C. is reported. However, the addition of oxygen atoms between the methyl groups and the silicon atom of the ligand is still experimental. That is, the method has not been refined for production environments. There is concern that a precursor having a heavier molecular weight, due to the addition of three oxygen atoms to the methyl groups, may require high bubbler temperatures to vaporize. Unexpected premature decomposition problems may result as higher vaporization temperatures and lower system pressures are required. It is also possible that the symmetry of the ligand molecules may tend to cause the precursor to solidify at room temperature. Further enhancement in the temperature stability of $Cu^{+1}$ precursors is desirable, and the use of other ligands to improve stability remains an area of ongoing research.

A Cu precursor comprising a ligand of methoxy and methyl groups is disclosed in co-pending application Serial No. 08/779,640, filed Jan. 7, 1997, entitled "Precursor with (Methoxy)(methyl)silylolefin Ligands to Deposit Cu and Method for Same", invented by Senzaki et al., Attorney Docket No. SMT 252, and assigned to the same assignee as the instant patent. The disclosed precursor permits either one or two methoxy groups to be bonded to the silicon atom of the ligand. That is, the precursor can be "fine tuned" using ligands having more methoxy groups than tmvs, but less than tmovs are provided. The oxygen atoms in the methoxy groups contribute electrons to the Cu atoms, to strengthen the Cu-olefin bond, and so, prevent the premature decomposition of the precursor in storage, or as the precursor is heated for the application of Cu to an IC surface. However, only hydrocarbon groups of one carbon atom, $CH_3$ (methyl) and $OCH_3$ (methoxy), are disclosed.

It would be advantageous if a method were found of making a Cu(hfac) precursor stable over a wider range of temperatures, and to provide the precursor with a longer shelf life.

It would be advantageous if the ligand attached to the Cu(hfac) precursor would cleave at a consistent temperature. Additionally, it would be advantageous if the alkene ligand and the hfac would cleave at approximately the same temperature to yield consistent precursor decomposition.

It would be advantageous if the deposition temperature, or temperature at which the (hfac)Cu(ligand) compound decomposes, could be decreased to simplify commercial processes. At the same time, it would be advantageous if a high precursor vapor pressure could be maintained at these relatively low decomposition temperatures to deposit a thicker layer of copper on selected IC surfaces. Further, it would be advantageous if the vapor pressure of the precursor in the gas phase could be modified with different combinations of alkyloxy and alkyl groups.

It would also be advantageous if water, H-hfac, H-hfac dihydrate ($H-hfac \cdot 2H_2O$), and silylolefin ligand additives were no longer necessary to blend with a Cu precursor to improve the thermal stability of the Cu precursor, and to improve the conductivity and deposition rate of the deposited copper.

It would be advantageous if a (hfac)Cu(ligand) could be designed to more readily retain a liquid form at room temperature so as to simply precursor delivery in IC processes. Further, it would be advantageous if the viscosity of the liquid phase precursor could be modified with different combinations of alkyloxy and alkyl groups.

Accordingly, a volatile Cu precursor compound for the chemical vapor deposition (CVD) of Cu to selected surfaces is provided. The precursor compound comprises $Cu^{+1}$ (hexafluoroacetylacetonate), or $Cu^{+1}$(hfac), and a silylolefin ligand including at least one ethoxy group bonded to the silicon atom, with any remaining bonds to the silicon atom being made to ethyl groups. That is, one of the three single bonds to the silicon atom of the ligand is made to an ethoxy group. The electron donation capability of the oxygen in the ethoxysilylolefin ligand provide a secure bond between the Cu and the ethoxysilylolefin ligand as the compound is heated to vaporization temperature. Prior art precursors have typically used methyl and methoxy groups bonded to silicon.

In one preferred embodiment, three ethoxy groups are bonded to the silicon atom, yielding triethoxyvinylsilane (teovs), whereby the three oxygen atoms of the triethoxy group donate electrons to Cu to increase the temperature stability of the precursor. In another preferred embodiment, two ethoxy groups and one ethyl group are bonded to the silicon atom, yielding diethoxyethylvinylsilane (deoevs), whereby the two oxygen atoms of the diethoxyethyl group donate electrons to Cu to increase the temperature stability of the precursor. In another preferred embodiment, one ethoxy group and two ethyl groups are bonded to the silicon atom, yielding ethoxydiethylvinylsilane (eodevs), whereby the molecular weight of the oxygen atom of the ethoxyethyl group minimally suppresses the precursor volatility. Therefore, a ligand providing oxygen atom electrons from either one, two, or three, ethoxy groups is disclosed.

A volatile Cu precursor compound is also provided comprising $Cu^{+1}$(hfac), and a silylolefin ligand including at least one alkyloxy group, having at least two carbon atoms, bonded to the silicon atom. That is, the ligand contains an alkyloxy group from the group consisting of ethoxy, propoxy, butoxy, pentyloxy, hexyloxy, heptyloxy, and octyloxy. The electron donation capability of the oxygen in said alkyloxysilylolefin ligand provides a secure bond between the Cu and the alkyloxysilylolefin ligand as the compound is heated to vaporization temperature. A preferred embodiment further includes alkyl groups bonded the silicon atom of the ligand, in addition to alkyloxy groups.

A preferred embodiment further includes an addition to the compound to create a precursor blend. The precursor blend further comprises a water vapor having a vacuum partial pressure. The water vapor is blended with the precursor so that the partial pressure of the water vapor is generally in the range of 0.5 to 5% of the precursor partial pressure, whereby the addition of water vapor to the precursor increases the rate of Cu deposition.

A method for applying chemical vapor deposition (CVD) Cu on a selected surface is also provided, comprising the steps of: a) exposing each selected Cu-receiving surface to a volatile Cu precursor compound including $Cu^{+1}(hfac)$ and a silylolefin ligand, the ligand includes at least one ethoxy group bonded to the silicon atom, with any remaining bonds to the silicon atom being made to ethyl groups, during this step the precursor has a predetermined vacuum pressure; and b) while continuing to carry out step a), depositing Cu on each Cu-receiving surface. The bond between the ethoxysilylolefin ligand and Cu prevents the decomposition of the precursor at low temperatures. A method for applying CVD Cu using a silylolefin ligand including at least one alkyloxy group, having at least two carbon atoms, bonded to the silicon is also provided.

DETAILED DESCRIPTION OF THE PREFERRED EMBODIMENT

Figure 1:
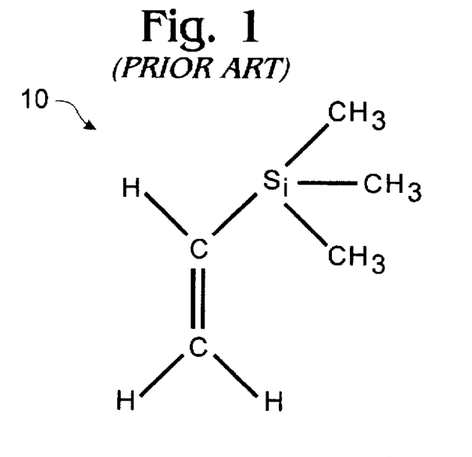
FIG. 1 is a schematic representation of the tmvs ligand (prior art).

FIG. 1 is a schematic representation of the tmvs ligand 10 (prior art). The double lines between the two carbon atoms represent double bonds, while the single lines between the remaining atoms represent, weaker, single bonds. Cu becomes attached to tmvs ligand 10 through the carbon atoms. Cu and hfac form a relatively secure bond, and the resulting $Cu^{+1}(hfac)^{-1}$ complex has no net electrical charge. As is well known in the art, atoms or complexes having opposite charges combine to form very stable complexes. The bonding between the $Cu^{+1}(hfac)^{-1}$ complex, hereafter called Cu(hfac) or (hfac)Cu, and ligand 10 is relatively weak due to lack of opposing net charges. For this reason, tmvs ligand 10 is first to cleave from the Cu precursor as it is vaporized and applied to a target surface. While not intending to be bound by theory, it is believed that if the ligand were able to provide more electrons, the bond between the ligand and the Cu(hfac) could be improved, resulting in a Cu precursor with improved temperature stability.

Figure 2:
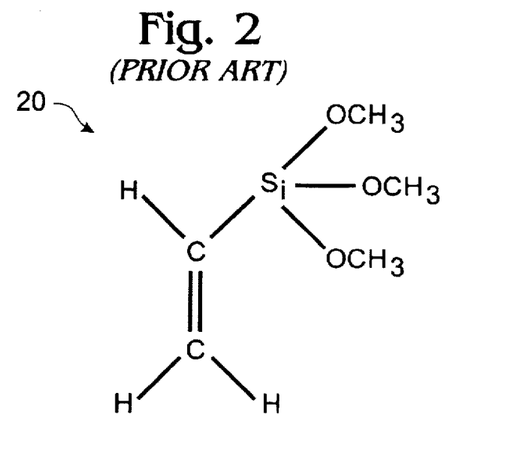
FIG. 2 is a schematic representation of the tmovs ligand (prior art).

FIG. 2 is a schematic representation of the tmovs ligand 20 (prior art). The difference between tmovs ligand 20 and tmvs ligand 10 of FIG. 1 is in the addition of three oxygen atoms to the three methyl groups to form three methoxy groups bound to the silicon atom. It is believed that the oxygen atoms of tmovs ligand 20 readily donate electrons to the Cu(hfac) complex, and so, allow tmovs ligand 20 to more tightly bind itself to Cu(hfac). There exist a variety of models to explain the bonding between the double bond carbon atoms and the Cu atom; the quantitative bonding process is not entirely understood. The higher molecular weight of the three additional oxygen atoms will typically result in higher vaporization temperatures. An increase in the vaporization temperature of the precursor, without a corresponding increase in temperature stability, results in a precursor with inconsistent Cu decomposition characteristics which, in turn, cause Cu deposition problems. The present invention was invented in response to the need for a precursor that could be modified to adjust the number of oxygen atoms, and the type of hydrocarbon groups, comprising the ligand.

Figure 3A:
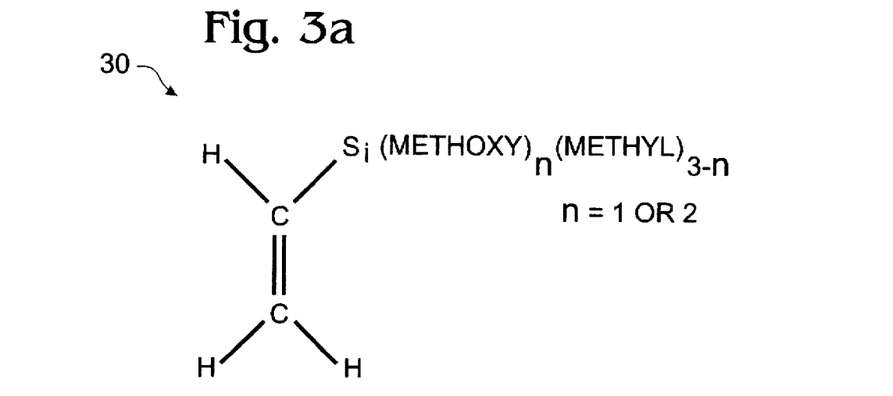
FIG. 3a is a schematic representation of the Cu precursor with (methoxy)(methyl) ligand of co-pending patent application Ser. No. 08/779,640, Attorney Docket No. SMT 252.

FIG. 3a is a schematic representation of the (methoxy) (methyl) ligand 30 of co-pending patent application Ser. No. 08/779,640 entitled "Precursor with (Methoxy)(methyl) silylolefin Ligands to Deposit Cu and Method for Same", invented by Senzaki et al., Attorney Docket No. SMT 252. This invention is invented to bridge the gap between ligand 10 (FIG. 1) with three methyl groups ($CH_3$), and ligand 20 (FIG. 2) with three methoxy groups ($OCH_3$). Ligand 30 includes at least one methoxy group bonded to the silicon atom. The electron donation capability of the oxygen in the (methoxy)(methyl)silylolefin ligand provides a secure bond between the Cu and the (methoxy)(methyl)silylolefin ligand as the compound is heated to vaporization temperature.

Figure 3B:
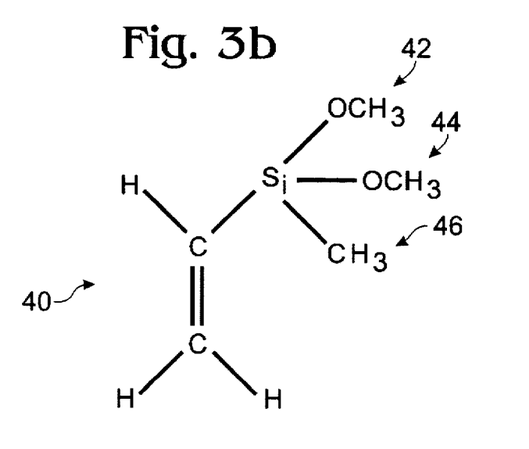
FIG. 3b is a schematic representation of an embodiment of the (methoxy)(methyl)silylolefin ligand of FIG. 3a, where the ligand is a dimethoxymethylvinylsilane (dmomvs) ligand.

FIG. 3b is a schematic representation of an embodiment of (methoxy)(methyl)silylolefin ligand 30 of FIG. 3a, where the ligand is a dimethoxymethylvinylsilane (dmomvs) ligand 40. Ligand 40 includes two methoxy groups 42 and 44 (OCH$_3$), and one methyl group 46 (CH$_3$). The two oxygen atoms of the dimethoxymethyl group donate electrons to Cu to increase the temperature stability of the precursor.

Figure 3C:
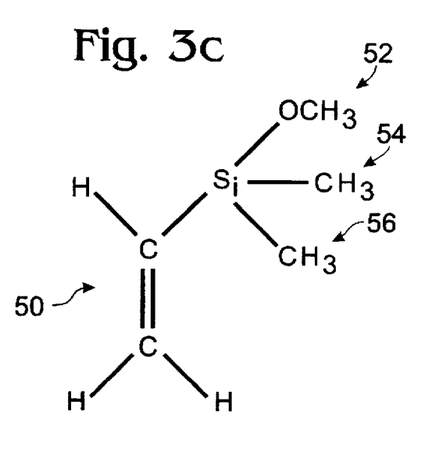
FIG. 3c is a schematic representation of another embodiment of the (methoxy)(methyl)silylolefin ligand of FIG. 3a, where the ligand is a methoxydimethylvinylsilane (modmvs) ligand.

FIG. 3c is a schematic representation of another embodiment of (methoxy)(methyl)silylolefin ligand 30 of FIG. 3a, where the ligand is a methoxydimethylvinylsilane (modmvs) ligand 50. Ligand 50 includes one methoxy group 52 and two methyl groups 54 and 56. The single oxygen atom of the methoxydimethyl group minimally suppresses the precursor volatility, since ligand 50 has a relatively small molecular weight compared to the ligands 30 (FIG. 3a) and 40 (FIG. 3b).

Figure 4A:
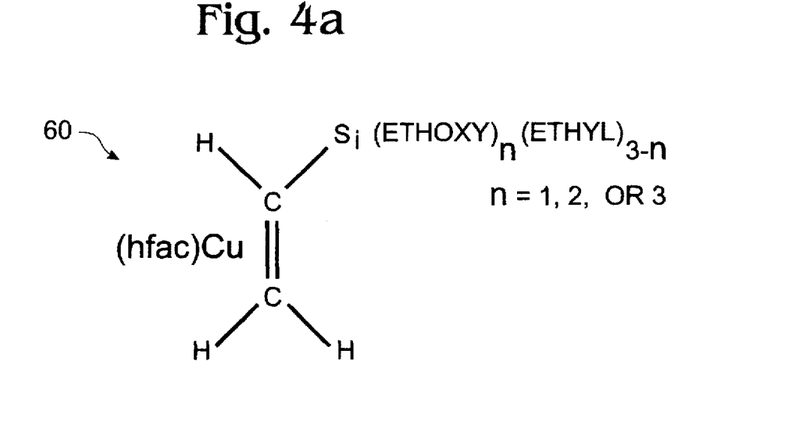
FIG. 4a is a schematic representation of the volatile Cu precursor compound of the present invention, using an (ethoxy)(ethyl)silylolefin ligand, for the chemical vapor deposition (CVD) of Cu to selected surfaces.

FIG. 4a is a schematic representation of the volatile Cu precursor compound 60 of the present invention, using an (ethoxy)(ethyl)silylolefin ligand, for the chemical vapor deposition (CVD) of Cu to selected surfaces. Precursor compound 60 comprises Cu+$^1$(hfac), and a silylolefin ligand including at least one ethoxy group (OC$_2$H$_5$) bonded to the silicon atom. The remaining bonds to the silicon atom are made to ethyl groups (C$_2$H$_5$). That is, the three hydrocarbon groups bonded to the silicon are one of the following combinations: 3 ethoxy groups, 2 ethoxy groups and 1 ethyl group, or 1 ethoxy group and 2 ethyl groups. The electron donation capability of the oxygen in the ethoxysilylolefin ligand provides a secure bond between the Cu and the ethoxysilylolefin as compound 60 is heated to vaporization temperature. The electron donation capability of the long carbon chain ethyl groups also helps provide a secure bond between the ligand and the Cu.

Figure 4B:
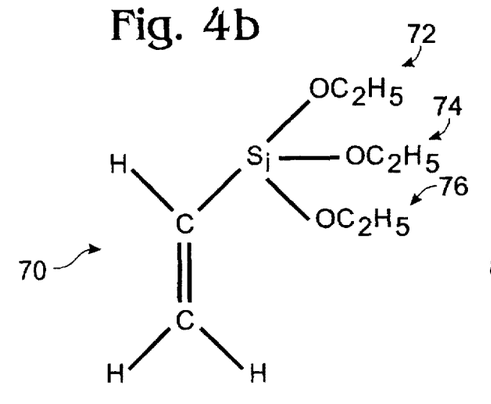
FIG. 4b is a schematic representation of a preferred embodiment of the precursor of FIG. 4a, where the (ethoxy)(ethyl)silylolefin ligand is a triethoxyvinylsilane (teovs) ligand.

FIG. 4b is a schematic representation of a preferred embodiment of precursor 60 of FIG. 4a, where the (ethoxy)(ethyl)silylolefin ligand is a triethoxyvinylsilane (teovs) ligand 70. Three ethoxy groups (OC$_2$H$_5$) 72–76 are bonded to the silicon atom, yielding teovs. The three oxygen atoms of the triethoxy group donate electrons to Cu to increase the temperature stability of compound 60.

Figure 4C:
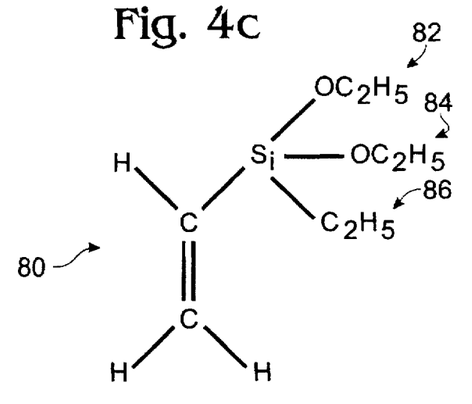
FIG. 4c is a schematic representation of another preferred embodiment of the precursor of FIG. 4a, where the (ethoxy)(ethyl)silylolefin ligand is a diethoxyethylvinylsilane (deoevs) ligand.

FIG. 4c is a schematic representation of another preferred embodiment of precursor 60 of FIG. 4a, where the (ethoxy) (ethyl)silylolefin ligand is a diethoxyethylvinylsilane (deoevs) ligand 80. Two ethoxy groups 82–84 and one ethyl group 86 are bonded to the silicon atom, yielding deoevs. The two oxygen atoms of the diethoxyethyl group donate electrons to Cu to increase the temperature stability of precursor 60. Ligand 80 has fewer oxygen atoms than ligand 70, and therefore, fewer electrons to donate. However, the molecular weight of ligand 80, for the same reason, is less than ligand 70. The ability to adjust the molecular weight of compound 60 is useful is adjusting the vaporization temperatures and vacuum pressures of precursor 60 to fit specific process requirements.

Figure 4D:
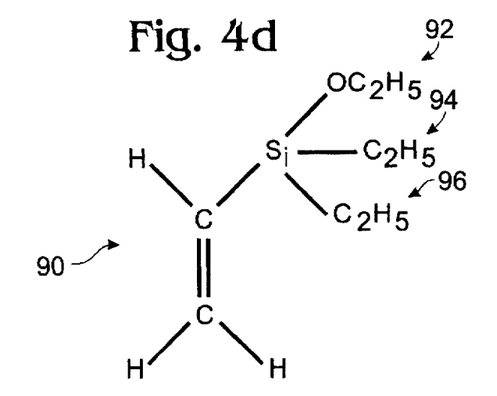
FIG. 4d is a schematic representation of another preferred embodiment of the precursor of FIG. 4a, where the (ethoxy)(ethyl)silylolefin ligand is a ethoxydiethylvinylsilane (eodevs) ligand.

FIG. 4d is a schematic representation of another preferred embodiment of precursor 60 of FIG. 4a, where the (ethoxy) (ethyl)silylolefin ligand is a ethoxydiethylvinylsilane (eodevs) ligand 90. One ethoxy group 92 and two ethyl groups 94 and 96 are bonded to the silicon atom, yielding eodevs. The molecular weight of the oxygen atom of the ethoxydiethyl group minimally suppresses the precursor volatility. Of the three combinations of ethoxy and ethyl groups depicted in FIGS. 4b–4d, ligand 90 has the smallest molecular weight.

Figure 5:
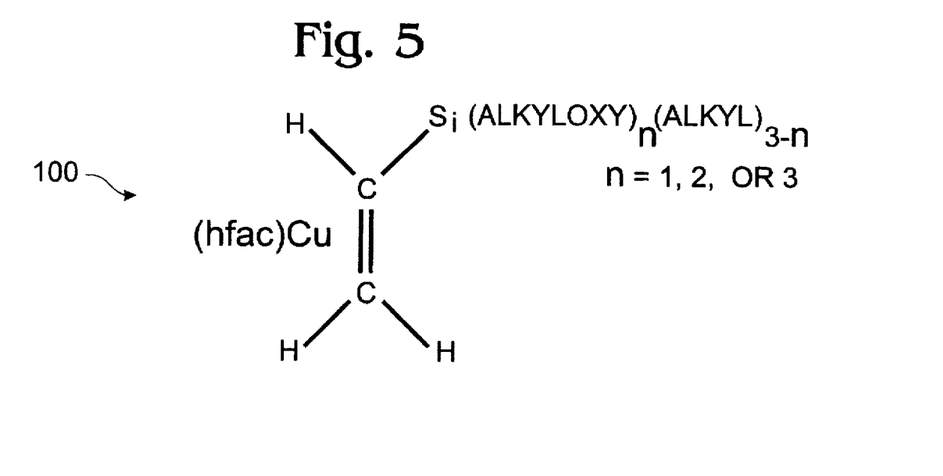
FIG. 5 is a schematic representation of the volatile Cu precursor compound of the present invention, using an (alkyloxy)(alkyl)silylolefin ligand, for the chemical vapor deposition (CVD) of Cu to selected surfaces.

FIG. 5 is a schematic representation of the volatile Cu precursor compound 100 of the present invention, using an (alkyloxy)(alkyl)silylolefin ligand, for the chemical vapor deposition (CVD) of Cu to selected surfaces. Precursor compound 100 comprises Cu+$^1$(hfac), and a silylolefin ligand including at least one alkyloxy group, having at least two carbon atoms, bonded to the silicon atom. Hydrocarbon groups are generally organized into groups that include 1 through 8 carbon atoms, also represented herein as C1–C8. Alkyloxy groups are hydrocarbons that additionally include oxygen atoms. FIG. 5 represents alkyloxy groups having either 2, 3, 4, 5, 6, 7, or 8 carbon atoms (C2–C8). That is, the alkyloxy groups consist of ethoxy, propoxy, butoxy, pentyloxy, hexyloxy, heptyloxy, and octyloxy. In addition, the alkyloxy groups consist of aryloxy groups, including phenyloxy. Further, when two or three alkyloxy groups are bonded to the silicon atom, some embodiments include alkyloxy groups with different numbers of carbon atoms. For example, in one preferred embodiment, ligand 100 includes an ethoxy group and a propoxy group. The electron donation capability of the oxygen in the alkyloxysilylolefin ligand provides a secure bond between the Cu and the alkyloxysilylolefin ligand as the compound is heated to vaporization temperature. In the preferred embodiment, the alkyloxy groups further include methoxy (C1) when at least one other alkyloxy group, having at least two carbon atoms, is bonded to the silicon atom. That is, when two alkyloxy groups are present, one of the alkyloxy groups, in some embodiments, is methoxy. When three alkyloxy groups are present, some embodiments include one methoxy group, and other embodiments include two methoxy groups.

Ligand 100 further includes alkyl groups bonded to the silicon atom. That is, both alkyloxy and alkyl groups are bound to the silicon atom, with at least one group being an alkyloxy group. Alkyl groups generally have 1, 2, 3, 4, 5, 6, 7, or 8 carbon atoms (C1–C8). That is, the alkyl groups consist of methyl, ethyl, propyl, butyl, pentyl, hexyl, heptyl, and octyl. The alkyl groups also consist of aryl groups including phenyl. Further, when two alkyl groups are bonded to the silicon atom, some embodiments include alkyl groups with different numbers of carbon atoms. For example, in one preferred embodiment, ligand 100 includes an ethyl group and a propyl group. In some embodiment alkyl groups and alkyloxy groups bonded to the same silicon atom also have different numbers of carbon atoms. For example, an ethoxy group is included with a propyl group.

Alternately stated, Cu precursor compound 100 of FIG. 5 has the following structural formula:

in which the X groups include at least one C2–C8 alkyloxy group. The electron donation capability of the oxygen in the alkyloxy groups provides a secure bond between the Cu and the H$_2$C=C(H)SiX$_3$ ligand, as compound 100 is heated to vaporization temperature.

In a preferred embodiment, the X groups are three ethoxy groups 72–76, as depicted in FIG. 4b. In another embodiment, the X groups are two ethoxy groups 82–84 and one ethyl group 86, as depicted in FIG. 4c. In one embodiment the X groups are one ethoxy group 92 and two ethyl groups 94–96, as depicted in FIG. 4d. A complete listing of all the alkyloxy/alkyl group combinations possible under the above structural formula is quite long and well known to those skilled in the art. Therefore, these other specific embodiments under the formula will not be listed herein.

In the preferred embodiment, the X groups further include C1 (methoxy) alkyloxy groups when at least one X group is a C2–C8 alkyloxy group. In one of these embodiments the X groups are two ethoxy groups and one methyl group. In another embodiment, the X groups are one ethoxy group and two methyl groups. In one embodiment the X groups are two methoxy groups and one ethyl group, in another, the X groups are one methoxy group and two ethyl groups. Once again, the full list of possible combinations is long and obvious to those skilled in the art.

As is well known in the art, alkyl and alkyloxy groups are generally arranged in either straight chains, branched chains, or cyclic chains, although combination chain arrangements also exist. In addition, the chains include both single bond and double bond arrangements between carbon atoms to form saturated and unsaturated groups of alkyls and alkyloxys. FIG. 5 represents all these possible (alkyloxy)(alkyl) variations. Likewise, the X groups are saturated and unsaturated straight carbon chains, and saturated and unsaturated branched carbon chains. X groups also include C3–C8 cyclic alkyl and aryl groups, as well as C3–C8 cyclic alkyloxy and aryloxy groups. These cyclic X groups chains are saturated and unsaturated.

In the preferred embodiment, compound 100 of FIG. 5 includes an additive to create a precursor blend. While not intending to be bound by theory, it is believed that organic components, such as silylolefins, H-hfac, and H-hfac dihydrate decrease precursor viscosity, making control over the flow of a precursor more precise. The precursor blend further comprises water vapor having a vacuum partial pressure as it is blended with precursor compound 100. The water vapor is blended with precursor 100 so that the partial pressure of said water vapor is generally in the range of 0.5 to 5% of precursor 100 partial pressure. Precursor 100 partial pressure is the percentage of the entire system pressure that is a result of the pressure of compound 100 after it is volatilized and mixed with a carrier gas. The addition of said water vapor to precursor 100 increases the rate of Cu deposition.

As disclosed in co-pending application Serial No. 08/745, 562, filed Nov. 8, 1996, entitled "Cu(hfac)TMVS Precursor With Water Additive To Increase The Conductivity Of Cu And Method For Same", invented by Nguyen et al., Attorney Docket No. SMT 244, the addition of water to a Cu(hfac) precursor, in the proper amounts, increases the deposition rate and the electrical conductivity of the deposited Cu. Using the methods disclosed in the above patent application, the deposition rates of Cu are improved with minimal degradation of the Cu conductivity. Refinements in the process will likely yield a precursor blend with further improvements in the deposition rate and electrical conductivity.

Figure 6:
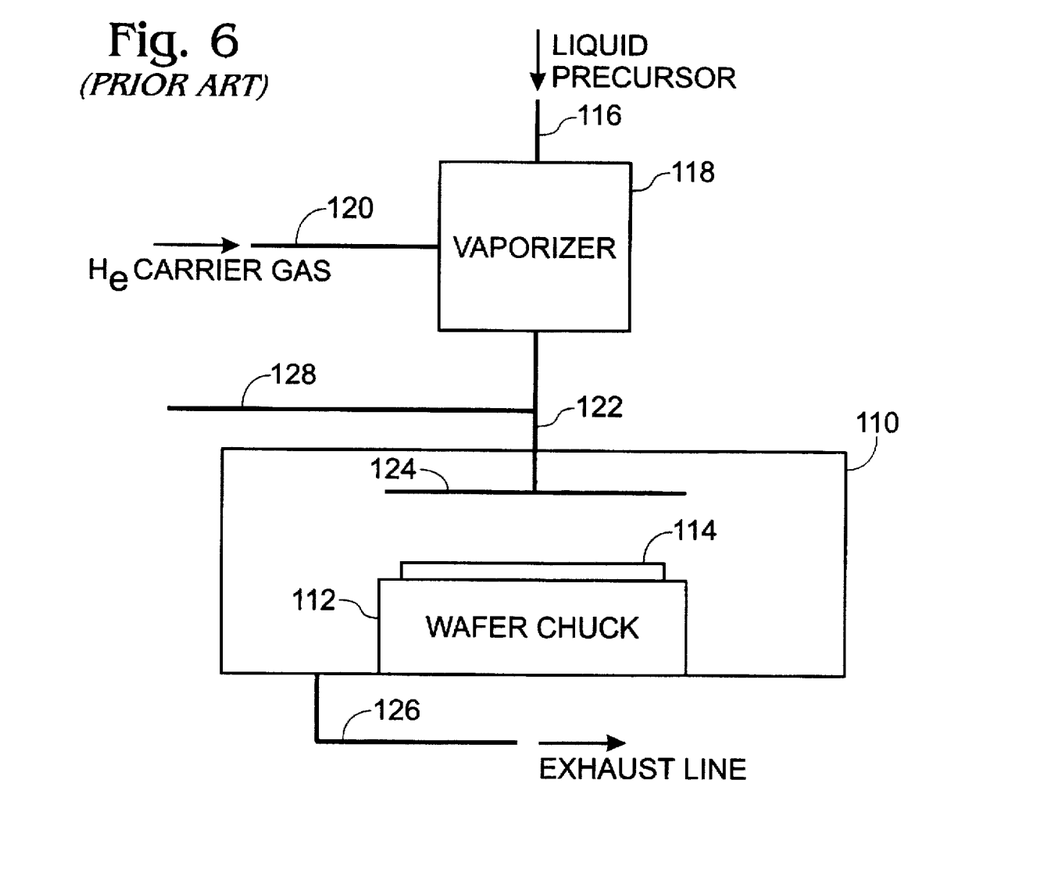
FIG. 6 is a block diagram of apparatus suitable to deposit Cu, with the precursor of the present invention, to selected surfaces (prior art).

FIG. 6 is a block diagram of apparatus suitable to deposit Cu, with the precursor of the present invention, to selected surfaces (prior art). An environmental chamber 110 is capable of maintaining a pressurized environment. Inside chamber 110 is a wafer chuck 112, and upon wafer chuck 112 is an IC, or wafer, having a selected, or Cu-receiving, surface 114. Cu precursor, in its liquid form, is introduced into line 116, and then into vaporizer 118, where the precursor is heated until it is volatile. Helium, or some other inert carrier gas, is introduced into line 120, and then into vaporizer 118, where it is mixed with the volatile precursor. The volatile precursor and carrier gas are carried through a line 122 to chamber 110. Inside chamber 110 the precursor/carrier gas mixture is dispersed through a showerhead 124, or some other equivalent gas dispersal means. Exhaust gases exit chamber 110 through a line 126. Line 126 is connected to a pump (not shown) to maintain a predetermined vacuum pressure in chamber 110.

Line 128 is used to introduce additives to the volatile precursor, typically the additives are in a volatile or gaseous form. The water vapor additive, mentioned above in discussing FIG. 5, is typically introduced through line 128. Alternately, additives are pre-packaged in the liquid precursor, or mixed with the liquid precursor compound in line 116.

The Cu precursor in line 116 is vaporized, in vaporizer 118, at a temperature generally in the range between 40° C. and 80° C. The Cu precursor in line 122 applied, through showerhead 124, to each selected surface 114 has a temperature generally in the range between 40° C. and 80° C. The Cu precursor is delivered in line 122 to each selected surface 114 with an inert gas. The inert gas, introduced in line 120, has a vacuum partial pressure generally in the range of 50% to 1000% of the precursor partial pressure.

Other materials are added to the Cu precursor compound in either its liquid form in line 116, or in a vapor form on line 128, to enhance particular characteristics of the precursor. In one embodiment, the compound includes an additive to create a precursor blend, with the precursor blend further comprising less than approximately 5% hexafluoroacetylacetone (H-hfac), as measured by weight ratio of the precursor compound. The H-hfac additive facilitates a Cu disproportionation reaction which enhances the Cu deposition rate. The disproportionation reaction causes the $(hfac)^{-1}Cu^{+1}$ to reconfigure the Cu atoms into either $Cu^{+0}$ or $Cu^{+2}$ atoms. The uncharged Cu atoms become deposited on the selected surface, as an $(hfac)_2Cu^{+2}$ complex and the ligand exit the process as exhaust gases in line 126.

One of the primary advantages of the present invention is how well it works as a pure compound, without any water, $H\text{-hfac-}2H_2O$, H-hfac, or silylolefin ligand additives. Such additives, when added to Cu precursor compounds, significantly increase the cost and difficulty of making the precursor. However, there is a need to maximize the stability, efficiencies, and deposition rates for Cu precursors in the production environment. Therefore, at least some amount of additives are likely to be blended with the precursor of the present invention. In one preferred embodiment, the precursor compound includes an additive to create a precursor blend, in which the precursor blend further comprises less than approximately 10% silylolefins, as measured by weight ratio of the precursor compound. The silylolefins are added to prevent the Cu from prematurely decomposing as the precursor is heated. The additional silylolefins help stabilize the precursor, if the ligand prematurely cleaves, by forming bonds with (hfac)Cu. The silylolefins are selected from the group consisting of trimethylvinylsilane (tmvs), dimethoxymethylvinylsilane (dmomvs), methoxydimethylvinylsilane (modmvs), trimethoxyvinylsilane (tmovs), triethoxyvinylsilane (teovs), ethoxymethoxymethylvinylsilane (eomomvs), diethoxymethylvinylsilane (deomvs), diethoxymethoxyvinylsilane (deomovs), ethoxydimethoxyvinylsilane (eodmovs), ethoxydiethylvinylsilane (eodevs), diethoxyethylvinylsilane (deoevs), dimethoxyethylvinylsilane (dmoevs), ethoxydimethylvinylsilane (eodmvs), methoxydiethylvinylsilane (modevs), and ethylmethoxymethylvinylsilane (emomvs). Methyl and ethyl (alkyloxy)(alkyl) combinations are listed above. A complete listing of all C1–C8 combinations would be burdensome to the reader and is obvious to those skilled in the art. The (alkyloxy) (alkyl) combination include saturated and unsaturated straight, branched, and cyclic carbon chain arrangements. Combination carbon chain arrangements are also included.

Alternately, compound 100 of FIG. 5 includes an additive to create a Cu precursor blend, the blend further comprising silylolefins having the following structural formula:

$$H_2C=C(H)SiX_3$$

in which each X group is selected from C1–C8 alkyloxy groups and C1–C8 alkyl groups. That is, the X groups may be all alkyloxy groups, all alkyl groups, or combinations of both. The possible alkyl groups include methyl (C1), ethyl (C2), propyl (C3), butyl (C4), pentyl (C5), hexyl (C6), heptyl (C7), octyl (C8) groups, aryl groups, or combinations of these alkyl groups. Likewise, the possible alkyloxy groups include methoxy (C1), ethoxy (C2), propoxy (C3), butoxy (C4), pentyloxy (C5), hexyloxy (C6), heptyloxy (C7), octyloxy (C8) groups, aryloxy groups or combinations of these alkyloxy groups. As mentioned above, combination carbon chain arrangements are also included.

In one embodiment, the precursor compound includes an additive to create a precursor blend, the blend further comprises less than approximately 5% H-hfac-2H$_2$O, as measured by weight ratio of the precursor compound, to increase the deposition rate of Cu. As noted above, the addition of water to the precursor generally increases the deposition rate of Cu on a selected surface.

In one embodiment, the precursor compound includes an additive to create a precursor blend, the blend further comprises less than approximately 0.4% H-hfac.2H$_2$O, as measured by weight ratio of the precursor compound, and less than approximately 5% silylolefins, as measured by weight ratio of the precursor compound, to increase the deposition rate of Cu. The additional silylolefins help stabilize the precursor as it is heated.

Figure 7:
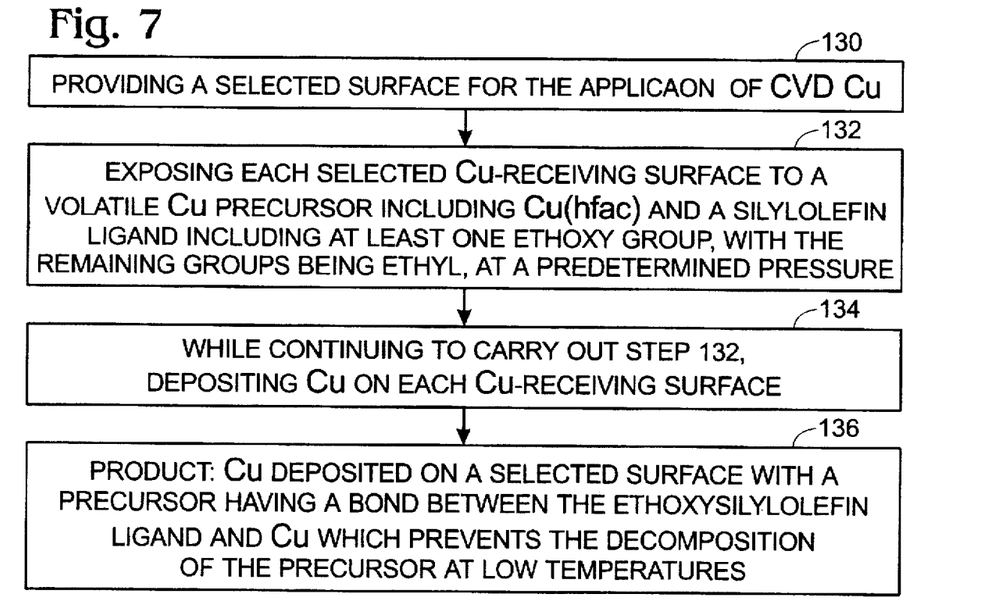
FIG. 7 illustrates steps in the method of applying CVD Cu, using the (ethoxy)(ethyl)silylolefin ligand, on a selected surface.

FIG. 7 illustrates steps in the method for applying CVD Cu, using the (ethoxy)(ethyl)silylolefin ligand, on a selected surface. Step 130 provides a selected surface for the application of CVD Cu. Step 132 exposes each selected Cu-receiving surface to a volatile Cu precursor compound including Cu+$^1$(hfac) and a silylolefin ligand including at least one ethoxy group bonded to the silicon atom, with any remaining bonds to the silicon atom being made to ethyl groups. The precursor is applied at a predetermined vacuum pressure. Step 134, while continuing to carry out Step 132, deposits Cu on each Cu-receiving surface. Step 136 is a product, Cu deposited on a selected surface with a precursor having a bond between the ethoxysilylolefin ligand and Cu which prevents the decomposition of the precursor at low temperatures. While it is desirable to deposit Cu at relatively low temperatures (below 200° C.), it is not desirable that the precursor begins the decomposition process at room storage temperatures or process delivery temperatures.

Figure 8:
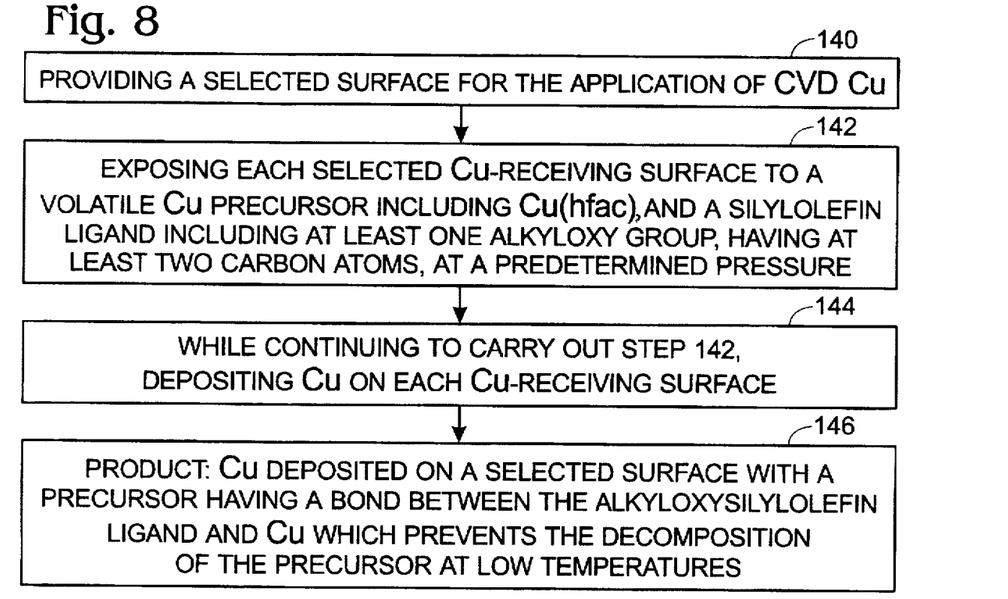
FIG. 8 illustrates steps in the method of applying CVD Cu, using a precursor including an (alkyloxy)(alkyl) silylolefin ligand, on a selected surface.

FIG. 8 illustrates steps in the method for applying CVD Cu, using the (alkyloxy)(alkyl)silylolefin ligand, on a selected surface. Step 140 provides a selected surface for the application of CVD Cu. Step 142 exposes each selected Cu-receiving surface to a volatile Cu precursor compound including Cu$^{+1}$(hfac) and a silylolefin ligand including at least one alkyloxy group, having at least two carbon atoms, bonded to the silicon. The precursor is applied at a predetermined vacuum pressure. Step 144, while continuing to carry out Step 142, deposits Cu on each Cu-receiving surface. Step 146 is a product, Cu deposited on a selected surface with a precursor having a bond between the alkyloxysilylolefin ligand and Cu which prevents the decomposition of the precursor at low temperatures.

The preferred embodiment includes the further step of, simultaneously with Step 142, exposing each selected Cu-receiving surface to water vapor at a vacuum partial pressure generally in the range between 0.5 and 5% of the precursor partial pressure. The addition of water vapor to the precursor increases the rate of Cu deposition.

The Cu-receiving, or selected surface, of the above method is equivalent to selected surface 114 in FIG. 6. Each Cu-receiving surface in Step 144 has a temperature generally in the range between 160° and 250° C., and the Cu precursor vapor applied to each selected surface 114 has a temperature generally in the range between 40° and 80° C. It is the relatively high temperature of the target surface that preferably causes the Cu precursor to decompose, and so deposit uncharged Cu atoms on the surface. Cu is deposited on each Cu-receiving surface in Step 144 for a time generally in the range between 100 and 1000 seconds. That is, the controlled deposition process occurs within 100 to 1000 seconds.

The Cu precursor of the present invention is prepared in accordance with methods suggested by prior art synthesis methods. For example, a suitable synthesis method is based on an approach taken by Doyle et al., in "Alkene and Carbon Monoxide Derivatives of Copper (I) and Silver (I) β-Diketonates", Organometallics, 1985, 4, pp. 830–835. The Cu precursor is obtained through the following reaction:

$$Cu_2O+2H\text{-}hfac+2L\rightarrow 2(hfac)CuL+H_2O$$

where L is the silylolefin ligand.

An (hfac)Cu(teovs) precursor was made in accordance with the above method. Teovs (0.68 mol) was added to a suspension of Cu$_2$O (0.34 mol) in 500 mL of tetrahydrofuran. H-hfac (0.68 mol) was added dropwise to this mixture at room temperature. The solution was stirred as the drops were added. The reaction mixture was stirred for two days. The unreacted Cu$_2$O was removed by filtration, and the solvent was removed under vacuum. The vacuum distillation of the product occurring at approximately 0.2 to 0.3 Torr at a bath temperature of 70°–75° C. 0.22 mol (32% yield) of precursor resulted.

Another suitable synthesis method is suggested by Norman et al., in U.S. Pat. No. 5,085,731. However, the yield of precursor made per the this method was lower than the method of Doyle et al.

Table 1 is a chart listing the deposition thickness and resistivity of Cu deposited using the precursor of the present invention and the apparatus depicted in FIG. 6. The teovs ligand embodiment of the invention was chosen for the experiment. The precursor was used to deposit Cu on a 6" diameter substrate covered with a 2000 Å thick layer of silicon dioxide deposited from tetraethoxysilane (TEOS oxide), which is in turn covered with a 500 Å thick layer of TiN. For the two depositions using (hfac)Cu(teovs) listed in Table 1, Cu-receiving surface 114 had a temperature of approximately 195° C. The deposition time for both depositions was approximately 600 seconds. The precursor flow rate in line 116 was approximately 0.5 cc/min. The vaporization temperature, in vaporizer 118, was approximately 70° C. Finally, the He carrier gas flow rate in line 120 was approximately 100 cc/min.

TABLE 1

| Chamber Pressure (Torr) | Water Additive (mT) | Thickness | Resistivity |
|---|---|---|---|
| 0.2 | 0 | ≈4600Å | 2.0μ-ohm-cm |
| 1.0 | 0 | ≈5500Å | 1.95μ-ohm-cm |

Table 2 is a chart listing comparing the deposited thicknesses, deposition times, and resistivities of a prior art Cu precursors. The precursors are as follows:

1) the original "Cupra Select" formula, a trademark of Schumacher, Carlsbad, Calif. 92009, or (hfac)Cu(tmvs);

2) (hfac)Cu(tmvs) with tmvs and H-hfac-2H$_2$O additives;

3) (hfac)Cu(tmvs) with water vapor per the method suggested in co-pending application Ser. No. 08/745,562, filed Nov. 8, 1996, entitled "Cu(hfac)TMVS Precursor With Water Additive To Increase The Conductivity Of Cu And Method For Same", invented by Nguyen et al., Attorney Docket No. SMT 244; and The various precursors of Table 2 were applied by the processes and apparatus generally depicted by FIG. 6. The total environmental pressure of chamber 110 was approximately 2.0 T (Torr). The precursor flow in line 116 was approximately 0.8 cc/min, and the flow rate of the He gas in line 120 was approximately 100 cc/min. The temperature of vaporizer 118 was approximately 70° C. when additives where used, and 50° C. for (hfac)Cu(tmvs) with no additives and (hfac)Cu(tmvs) with water. The vaporization temperature was reduced to approximately 50° C., as the precursor tends to decompose at higher temperatures. Selected surface 114 was a 6" diameter Si substrate covered with 2000 Å of TEOS oxide, which in turn, was covered with 500 Å of TiN. The temperature of the selected surface was approximately 195° C. The length of the deposition was optimized for the precursor used, generally between 150 and 700 seconds.

TABLE 2

|  | Thickness | Deposition Time | Resistivity |
|---|---|---|---|
| (hfac)Cu(tmvs) | ≈900Å | 700 sec. | >100μ-ohm-cm |
| (hfac)Cu(tmvs) + Additive | ≈3000Å | 150 sec. | ≈2μ-ohm-cm |
| (hfac)Cu(tmvs) + Water | ≈3000Å | 250 sec. | ≈1.8μ-ohm-cm |

In comparing Table 1 to Table 2, the results show the precursor of the present invention is able to provide thick depositions of Cu and excellent resistivities. Even better results are likely to be obtained after refinements in the process.

The precursor of the present invention discloses various combinations of alkyloxy groups and alkyl groups in the ligand which offer a wide range of improvements over prior art Cu precursors. The use of alkyloxy groups in the ligand increases the stability and shelf life of the precursor, since the electrons of the oxygen atoms are contributed to the Cu atom as the compound begins to decompose. Having the option of adjusting the ratio of alkyloxy groups to alkyl groups permits the user to select a precursor with the molecular weight optimal for a specific CVD process.

The use of carbon chains longer than the prior art use of methyl and methoxy, increases the electron donation capability of the ligand, as both the long chain (C2–C8) alkyloxy groups and the oxygen atoms contribute electrons to the Cu atom. Simmonds et al., in "A stable, liquid precursor for aluminum", Chemtronics, Vol. 5, 1991, pp. 155–158, suggest that the substitution of long chain carbons groups, such as ethyl, for methyl groups results a precursor compound with a lower melting point. While not intending to be bound by theory, it is believed that the asymmetry of the longer chains causes a lower melting point, and that the precursor of the present invention has a low melting point, more easily retaining liquid form at room temperature, as a result of the relatively long alkyl and alkyloxy hydrocarbon chains. A liquid CVD precursor is generally more capable of precise delivery and reproducibility in most CVD systems.

One of the main advantages of the precursor of the present invention is that good deposition rates, thermal stability, and Cu conductivity are obtainable without the necessity of blending the precursor with water and organic additives. However, alternate embodiments of the precursor permit it to be blended with water, silylolefins, H-hfac, H-hfac dihydrate, and combinations of additives to provide further enhancements. These additives are blended with the precursor in either its liquid or volatile state. Specific combinations of ethoxy and ethyl group in the ligand have been emphasized in the above specification. Other embodiments of the invention will occur to those skilled in the art.

What is claimed is:

1. A volatile copper (Cu) precursor compound for the chemical vapor deposition (CVD) of copper (Cu) to selected surfaces, the precursor compound comprising:

Cu$^{+1}$(hexafluoroacetylacetonate); and a silylolefin ligand including at least one ethoxy group bonded to the silicon atom, with any remaining bonds to said silicon atom being made to ethyl groups, whereby the electron donation capability of the oxygen in said ethoxysilylolefin ligand provides a secure bond between the Cu and said ethoxysilylolefin ligand as the compound is heated to vaporization temperature.

2. A Cu precursor as in claim 1 in which three ethoxy groups are bonded to said silicon atom, yielding triethoxyvinylsilane (teovs), whereby the three oxygen atoms of the triethoxy group donate electrons to Cu to increase the temperature stability of the precursor.

3. A Cu precursor as in claim 1 in which two ethoxy groups and one ethyl group are bonded to said silicon atom, yielding diethoxyethylvinylsilane (deoevs), whereby the two oxygen atoms of the diethoxyethyl group donate electrons to Cu to increase the temperature stability of the precursor.

4. A Cu precursor as in claim 1 in which one ethoxy group and two ethyl groups are bonded to said silicon atom, yielding ethoxydiethylvinylsilane (eodevs), whereby the molecular weight of the oxygen atom of the ethoxydiethyl group minimally suppresses the precursor volatility.

5. A volatile copper (Cu) precursor compound for the chemical vapor deposition (CVD) of copper (Cu) to selected surfaces, the precursor compound comprising:

Cu$^{+1}$(hexafluoroacetylacetonate); and a silylolefin ligand including at least one alkyloxy group, having at least two carbon atoms, bonded to the silicon atom, whereby the electron donation capability of the oxygen in said alkyloxysilylolefin ligand provides a secure bond between the Cu and said alkyloxysilylolefin ligand as the compound is heated to vaporization temperature.

6. A Cu precursor as in claim 5 wherein the compound includes an additive to create a precursor blend, the precursor blend further comprising:

water vapor having a vacuum partial pressure, said water vapor blended with the precursor so that the partial pressure of said water vapor is generally in the range of 0.5 to 5% of the precursor partial pressure, whereby the addition of said water vapor to the precursor increases the rate of Cu deposition.

7. A Cu precursor as in claim 5 further including alkyl groups bonded to said silicon atom, with said alkyl groups consisting of methyl, ethyl, propyl, butyl, pentyl, hexyl, heptyl, octyl, and aryl.

8. A Cu precursor as in claim 5 in which said alkyloxy groups consist of ethoxy, propoxy, butoxy, pentyloxy, hexyloxy, heptyloxy, octyloxy, and aryloxy.

9. A Cu precursor as in claim 5 in which said alkyloxy groups further include methoxy when at least one other alkyloxy group. having at least two carbon atoms. is bonded to said silicon atom.

10. A Cu precursor as in claim 5 in which the Cu precursor is vaporized at a temperature generally in the range between 40° C. and 80° C.

11. A Cu precursor as in claim 5 wherein the Cu precursor vapor applied to each selected surface has a temperature generally in the range between 40° C. and 80° C.

12. A Cu precursor as in claim 5 wherein the precursor is delivered to each selected surface with an inert gas, and in which the inert gas has a vacuum partial pressure generally in the range of 50% to 1000% of the precursor partial pressure.

13. A Cu precursor as in claim 5 wherein the compound includes an additive to create a precursor blend. and in which the precursor blend further comprises:

less than approximately 5% hexafluoroacetylacetone (Hhfac). as measured by weight ratio of the precursor compound. to facilitate a Cu disproportionation reaction which enhances the Cu deposition rate.

14. A Cu precursor as in claim 5 wherein the compound includes an additive to create a precursor blend. and in which the precursor blend further comprises:

less than approximately 10% silylolefins, as measured by weight ratio of the precursor compound. to prevent said Cu from prematurely decomposing as the precursor is heated.

15. A Cu precursor as in claim 14 in which said silylolefins are selected from the group consisting of trimethylvinylsilane (tmvs). dimethoxymethylvinylsilane (dmomvs). methoxydimethylvinylsilane (modmvs). trimethoxyvinylsilane (tmovs). triethoxyvinylsilane (teovs). ethoxymethoxymethylvinylsilane (eomomvs). diethoxymethylvinylsilane (deomvs). diethoxymethoxyvinylsilane (deomovs). ethoxydimethoxyvinylsilane (eodmovs). ethoxydiethylvinylsilane (eodevs). diethoxyethylvinylsilane (deoevs). dimethoxyethylvinylsilane (dmoevs). ethoxydimethylvinylsilane (eodmvs). methoxydiethylvinylsilane (modevs). and ethylmethoxymethylvinylsilane (emomvs).

16. A Cu precursor as in claim 5 wherein the compound includes an additive to create a precursor blend. and in which the blend further comprises:

less than approximately 5% Hhfac·2H$_2$O, as measured by weight ratio of the precursor compound, to increase the deposition rate of Cu.

17. A Cu precursor as in claim 5 wherein the compound includes an additive to create a precursor blend. and in which the blend further comprises:

less than approximately 0.4% Hhfac·2H$_2$O, as measured by weight ratio of the precursor compound, and less than approximately 5% silylolefins. as measured by weight ratio of the precursor compound. to increase the deposition rate of Cu.

18. A volatile copper (Cu) precursor compound for applying chemical vapor deposition (CVD) copper (Cu) to selected surfaces. the precursor compound having the following structural formula:

(hfac)Cu(H$_2$C=C(H)SiX$_3$)

in which the X groups include at least one C2–C8 alkyloxy group consisting of ethoxy propoxy. butoxy. pentyloxy. hexyloxy. heptyloxy. and octyloxy. whereby the electron donation capability of the oxygen in said alkyloxy groups provides a secure bond between the Cu and the H$_2$C=C(H)SiX$_3$ ligand. as the compound is heated to vaporization temperature.

19. A Cu precursor as in claim 18 in which said X groups are three ethoxy groups.

20. A volatile copper (Cu) precursor compound for applying chemical vapor deposition (CVD) copper (Cu) to selected surfaces, the precursor compound having the following structural formula:

(hfac)Cu(H$_2$C=C(H)SiX$_3$)

in which the X groups are two ethoxy groups and one ethyl group.

21. A volatile copper (Cu) precursor compound for applying chemical vapor deposition (CVD) copper (Cu) to selected surfaces. the precursor compound having the following structural formula:

(hfac)Cu(H$_2$C=C(H)Six$_3$)

in which the X groups are one ethoxy group and two ethyl groups.

22. A volatile copper (Cu) precursor compound for applying chemical vapor deposition (CVD) copper (Cu) to selected surfaces. the precursor compound having the following structural formula:

(hfac) Cu(H$_2$C=C(H)SiX$_3$)

in which the X groups include at least one C2–C8 alkyloxy group and in which said X groups further include C1 alkyloxy groups when at least one X group is a C2–C8 alkyloxy group.

23. A Cu precursor as in claim 22 in which said X groups are two ethoxy groups and one methyl group.

24. A Cu precursor as in claim 22 in which said X groups are one ethoxy group and two methyl groups.

25. A Cu precursor as in claim 22 in which said X groups are two methoxy groups and one ethyl group.

26. A Cu precursor as in claim 22 in which said X groups are one methoxy group and two ethyl groups.

27. A Cu precursor as in claim 22 in which said X groups include C3–C8 cyclic alkyl groups and C3–C8 cyclic alkyloxy groups.

28. A Cu precursor as in claim 22 in which the compound includes an additive to create a Cu precursor blend, the blend further comprising silylolefins having the following structural formula:

H$_2$C=C(H)SiX$_3$ in which each X group is selected from C1–C8 alkyloxy groups and C1–C8 alkyl groups.

29. A Cu precursor as in claim 22 wherein the precursor includes an additive to create a precursor blend, the precursor blend further comprising:

water vapor having a vacuum partial pressure, said water vapor blended with the precursor so that the partial pressure of said water vapor is generally in the range of 0.5 to 5% of the precursor partial pressure. whereby the addition of said water vapor to the precursor increases the rate of Cu deposition and the electrical conductivity of the deposited Cu.

* * * * *